US 6,602,544 B2

(12) United States Patent
Piselli

(10) Patent No.: US 6,602,544 B2
(45) Date of Patent: Aug. 5, 2003

(54) MINERAL COMPOUND COMPOSITE TEXTILE MATERIAL AND METHOD OF MANUFACTURING

(76) Inventor: Veronica Piselli, 297 Cedar St., South Hempstead, NY (US) 11550

(*) Notice: Subject to any disclaimer, the term of this patent is extended or adjusted under 35 U.S.C. 154(b) by 0 days.

(21) Appl. No.: 09/942,233

(22) Filed: Aug. 29, 2001

(65) Prior Publication Data
US 2003/0045195 A1 Mar. 6, 2003

(51) Int. Cl.[7] .................................................. B05D 5/00
(52) U.S. Cl. ..................... 427/128; 427/230; 427/434.6
(58) Field of Search .................................. 427/180, 201, 427/230, 434.6, 128

(56) References Cited

U.S. PATENT DOCUMENTS

| 223,019 | A | * | 12/1879 | Vaughan | 8/498 |
| 4,234,907 | A | * | 11/1980 | Daniel | 139/420 R |
| 4,284,664 | A | * | 8/1981 | Rauch, Sr. | 427/180 |
| 4,422,286 | A | * | 12/1983 | Simpson et al. | 57/217 |
| 4,667,462 | A | * | 5/1987 | Smyth | 57/217 |
| 4,748,366 | A | * | 5/1988 | Taylor | 310/311 |
| 4,960,430 | A | * | 10/1990 | Koerber et al. | 427/108 |
| 5,116,679 | A | * | 5/1992 | Nadkarni et al. | 423/291 |
| 5,143,583 | A | * | 9/1992 | Marchessault et al. | 162/138 |
| 5,201,169 | A | * | 4/1993 | Miyashita | 57/295 |
| 5,262,591 | A | * | 11/1993 | Aldissi | 174/106 SC |
| 5,426,716 | A | * | 6/1995 | Arroyo et al. | 385/100 |
| 5,468,529 | A | * | 11/1995 | Kwon et al. | 210/503 |
| 5,602,381 | A | * | 2/1997 | Hoshino et al. | 235/449 |
| 6,011,887 | A | * | 1/2000 | Kamei et al. | 385/100 |
| 6,096,666 | A | * | 8/2000 | Jachimowicz et al | 139/420 R |
| 6,120,531 | A | * | 9/2000 | Zhou et al. | 442/131 |
| 6,135,987 | A | * | 10/2000 | Tsai et al. | 264/165 |
| 6,139,959 | A | * | 10/2000 | Meraldi et al. | 428/364 |
| 6,195,798 | B1 | * | 3/2001 | Bachner, Jr. | 2/2.5 |

* cited by examiner

Primary Examiner—Michael Barr
Assistant Examiner—Kirsten Crockford Jolley
(74) Attorney, Agent, or Firm—Michael I. Kroll

(57) ABSTRACT

A composite fiber made from natural and/or synthetic fibers having mineral compounds such as gemstones, colors and wavelengths, piezoelectric crystals and magnets whereby said fabrics can be placed against the body, such as the longitudinal lines of acupuncture points called meridians, the chakra system and/or circulatory systems for the purpose of transporting and channeling energy. The methods of combining the gemstones with the natural/synthetic fibers include encasing the mineral compounds within the natural/synthetic fibers by bonding the mineral compounds to the natural/synthetic fibers or laminating the mineral compound or compounds to the natural/synthetic fiber.

3 Claims, 6 Drawing Sheets

MINERAL COMPOUND COMPOSITE TEXTILE MATERIAL AND METHOD OF MANUFACTURING

BACKGROUND OF THE INVENTION

1. Field of the Invention

The present invention relates generally to composite threads and, more specifically, to imbuing fabrics or cloths with mineral compounds such as gemstones, colors and wavelengths, piezoelectric crystals and magnets whereby said fabrics can be placed against the longitudinal lines of acupuncture points of the human body called meridians and chakras for the purpose of channeling vibratory energetic reactions.

2. Description of the Prior Art

There are other composite fibers designed for fabric manufacture. Typical of these is U.S. Pat. No. 223,019 issued to Vaughan on Dec. 30, 1879.

Another patent was issued to Daniel on Nov. 18, 1980 as U.S. Pat. No. 4,234,907. Yet another U.S. Pat. No. 4,667,462 was issued to Smyth on May 26, 1987 and still yet another was issued on May 31, 1988 to Taylor as U.S. Pat. No. 4,748,366.

Another patent was issued to Koerber et al. on Oct. 2, 1990 as U.S. Pat. No. 4,960,430. Yet another U.S. Pat. No. 5,116,679 was issued to Nadkarni et al. on May 26, 1992. Another was issued to Miyashita on Apr. 13, 1993 as U.S. Pat. No. 5,201,169 and still yet another was issued on Aug. 1, 2000 to Jachimowicz et al. as U.S. Pat. No. 6,096,666.

Another patent was issued to Zhou et al. on Sept. 19, 2000 as U.S. Pat. No. 6,120,531. Yet another U.S. Pat. No. 6,135,987 was issued to Tsai et al. on Oct. 24, 2000. Another was issued to Meraldi et al. on Oct. 31, 2000 as U.S. Pat. No. 6,139,959 and still yet another was issued on Mar. 6, 2001 to Bachner, Jr. as U.S. Pat. No. 6,195,798.

U.S. Pat. No. 223,019

Inventor: Henry V. Vaughan

Issued: Dec. 30, 1879

Discloses a method whereby infusorial earth is combined with a coloring agent and water or alcohol to form a colored powder when dried. The colored powder is further processed by mixing paraffine or other non-saponifiable oil dissolved with benzine or other solvent whereupon after drying the mixture is reduced to a tenacious powder. The powder is dusted onto raw preprocessed cotton, wool or other fiberous material and after passing through all the operations involved in manufacturing it into spun yarn the color-charged powder becomes thoroughly incorporated with the fiber.

U.S. Pat. No. 4,234,907

Inventor: Maurice Daniel

Issued: Nov. 18, 1980

A light emitting fabric (10) in which optical fibers (12, 28, 46, 48) are part of the weave, replacing some of the threaded fibers (27), whereby the fabric is uniformly illuminated and, accordingly, decorated. The individual optical fibers are gathered into a bundle (15) at one end of the fabric and illuminated by a light source (17). Light traveling through the fibers is emitted in small amounts throughout the lengths thereof through small scratches (14) that pierce the outer coating. Uniformity and intensity of light are enhanced by providing a reflective coating (13) on the non-illuminated ends of the optical fibers. This fabric is usable in clothing; such as costumes, high visibility safety clothing, suntan suits (21); rugs, draperies, theater curtains, architectural panels (23), fiberglass boat hulls, and the like.

U.S. Pat. No. 4,667,462

Inventor: Laurence C. Smyth

Issued: May 26, 1987

A method is provided for making a plastic-filled wire rope by preheating a lubricated wire rope to a temperature close to the melting point of the plastic material with which the rope is to be filled, and then injecting the plastic material in molten state under heat and pressure into the wire rope so as to fill essentially completely the interstices between the strands and the individual wires, while displacing and removing most of the lubricant initially present within the rope. The obtained novel plastic-filled, lubricated wire rope has improved wear and fatigue resistance as well as increased life.

U.S. Pat. No. 4,748,366

Inventor: George W. Taylor

Issued: May 31, 1988

An optical effect is produced in cooperation with the normal use of an article of manufacture, e.g., a toy such as a frisbee or a ball, or an article of clothing, such as a shoe, by mounting on the article a piezoelectric element for generating electrical energy in response to movement of the article and an optical effect device, such as a neon bulb, gas plasma, liquid crystal, or electroluminescent device, electrically connected to and energized by the element in response to such movement. In one embodiment, the element and device each comprises a thin, layer-like structure, the element and device structures being laminated or attached together.

U.S. Pat. No. 4,960,430

Inventor: Heinz Koerber et al.

Issued: Oct. 2, 1990

Mat and rough endless sheetlike, ribbon-shaped or filiform polymeric products, preferably natural-fiber-like mat and rough textile products of chemical fiber materials, in particular of synthetic fiber materials, or mat and rough polymer films with low transparency are produced by contacting endless sheetlike, ribbon-shaped or filiform polymeric products with fine particles of organic or inorganic solid matter. This gives the textile structures a rough, woolly, soft feel and they are mat, while films become rough and mat and have a low transparency.

U.S. Pat. No. 5,116,679

Inventor: Sadashiv K. Nadkarni

Issued: May 26, 1992

A process for producing fibres composed of or coated with carbides or nitrides. The process involves forming a first reaction zone containing microfine particles of an oxide (or oxide precursor) of silicon or a suitable metal (e.g. boron) uniformly mixed with carbon (or a carbon precursor); forming a second reaction zone comprising a layer having a thickness of 1 cm or less of a porous mass having a density of 1 g/cc or less formed of short or continuous fibres made of or coated with carbon (or carbon precursor); heating the first reaction zone in a non-oxidizing atmosphere to generate a gaseous sub-oxide of the silicon or metal; simultaneously heating the second reaction zone so that the gaseous sub-oxide diffuses into it and reacts with the carbon to form carbide or nitride on the fibres; and separating the resulting fibres from any carbide or nitride whiskers that may have formed in the second reaction zone. Short or continuous fibres (e.g. in the form of a fabric or paper-like sheets) consisting of or coated with carbides or nitrides can be formed in this way.

U.S. Pat. No. 5,201,169

Inventor: Toru Miyashita

Issued: Apr. 13, 1993

A fancy yarn has a plurality of metallic foil pieces wrapped around and attached to the surface of a yarn by an adhesive. The fancy yarn is manufactured by applying an adhesive to a yarn supplied from a supply bobbin, aerially holding the yarn under tension, attaching scattered metallic foil pieces to adhesive-applied regions of the yarn, twisting the yarn with the attached metallic foil pieces or generating swirling air streams around the yarn to wrap the yarn with the attached metallic foil pieces, and hardening the adhesive to secure the wrapped metallic foil pieces to the yarn. The fancy yarn with its surface made glossy by the attached foil pieces can simply be manufactured. A fancy yarn comprising a thin yarn wrapped with foil pieces can also be manufactured with ease. A woven fabric of high ornamental effect can be produced of the fancy yarn that is used as weft or warp threads.

U.S. Pat. No. 6,096,666

Inventor: Karen E. Jachimowicz

Issued: Aug. 1, 2000

A holographic textile fiber that selectively absorbs and reflects different wavelengths of light. A plurality of holographic textile fibers in combination forming a holographic textile fabric. The plurality of textile fibers characterized as including a central core including one of a light transmitting material, a light absorbing material, a light reflecting material, or a polymer dispersed liquid crystal (PDLC) material. The holographic textile fibers further including a plurality of layers of an optical media. Each of the plurality of layers having differing indices of refraction thereby forming a multi-layer interference coating overcoating the central core. The plurality of layers of optical media characterized as selectively reflecting particular wavelengths of light while transmitting differing wavelengths of light, thereby generating a plurality of interference patterns that form a holographic optical image as a result of an incident light.

U.S. Pat. No. 6,120,531

Inventor: Lin Zhou

Issued: Sep. 19, 2000

Fiber, fabric, clothes, and shoes having a material incorporated therein which, when stimulated by energy, emits a predetermined spectrum having a first electromagnetic radiation having a wavelength range selected from the group consisting of about 0.2 .mu.m to about 50 .mu.m, and about 0.4 .mu.m to about 25 .mu.m, and a second radiation having a wavelength range selected from the group consisting of about 7500 .mu.m to about 100,000 .mu.m, and about 5400 .mu.m to about 500,000 .mu.m, similar to radiation generated by the human body over similar ranges. A reflecting layer is adjacent to a fabric having the material incorporated therein such that body heat is conserved so as to achieve a therapeutic result. The energy stimulating the material can be body heat, electrical heat, magnetic energy, or other energy forms.

U.S. Pat. No. 6,135,987

Inventor: Fu-Jya Daniel Ysai

Issued: Oct. 24, 2000

A process is disclosed for forming a synthetic fiber including providing a first component of an aliphatic polyester polymer a second component of a multicarboxylic acid, mixing the first component aliphatic polyester polymer and the second component multicarboxylic acid to form an unreacted specified thermoplastic composition, and melt blending the unreacted specified thermoplastic composition in an extruder or a mixer. The second component multicarboxylic acid lubricates the extruder and provides a nucleating agent for crystallizing the specified thermoplastic composition to form a mean crystal size less than about 120 Angstroms. Fiber composed of the specified thermoplastic composition has a mean crystal size less than about 120 Angstroms. The fiber has a glass transition temperature (Tg) less than about 55.degree. C. In one aspect, a first component of polylactic acid and a second component of adipic acid provide synthetic fibers in a nonwoven structure used in a biodegradable and compostable disposable absorbent product for the absorption and removal of body fluids.

U.S. Pat. No. 6,139,959

Inventor: Jean-Paul Meraldi

Issued: Oct. 31, 2000

A cellulose formate fiber of liquid-crystal origin, having a high elongation at break and having the following characteristics: a) under an optical polarizing microscope, its filaments have a banded structure typical of its liquid-crystal origin; b) it satisfies the following relationships: DS.gtoreq.2; Ar.gtoreq.8; Te<45; Mi>500; Er>10, DS being the degree of substitution of the cellulose with formate groups in the fiber (in %), Ar the elongation at break (in %) of the fiber, Te its tenacity (in cN/tex), Mi its initial modulus (in cN/tex) and Er its energy at break (in J/g). Also, a process for obtaining this cellulose formate fiber by "dry-jet-wet-spinning" of a liquid-crystal solution of cellulose formate, in which water is used as coagulating agent. A fiber of cellulose regenerated from cellulose formate which itself has a high value of elongation at break, and a process for obtaining this fiber.

U.S. Pat. No. 6,195,798

Inventor: Thomas E. Bachner Jr.

Issued: Mar. 6, 2001

A ballistic resistant protective garment with a ballistic resistant pad having at least two panels and a plurality of overlying layered sheets within the panels of the ballistic resistant pad in which the sheets are constructed of woven lyotropic liquid crystal polymer fiber.

While these fibers may be suitable for the purposes for which they were designed, they would not be as suitable for the purposes of the present invention, as hereinafter described.

SUMMARY OF THE PRESENT INVENTION

A primary object of the present invention is to provide fabrics that can be used to make clothing or furniture coverings used by humans.

Another object of the present invention is to provide fabrics such as cotton, wool, silk or manmade fibers having mineral compounds, gemstones, and/or magnets forming an integral part of said materials.

Yet another object of the present invention is to provide a fabric that can be used to place magnets, gemstones, colors and wavelengths and/or piezoelectric crystals against the human body, such as the longitudinal lines of acupuncture points called the meridians and/or chakra system.

Still yet another object of the present invention is to provide a composite fiber containing silica quartz crystals that have been faceted, crushed and/ or powdered.

Another object of the present invention is to provide a composite fiber having natural fibers encompassing the crystal material.

Yet another object of the present invention is to provide a composite fiber having mineral compounds forming a sheath around natural and/or synthetic fibers.

Still yet another object of the present invention is to provide a composite fiber having mineral compounds speckled onto natural and/or synthetic fibers forming an integral part therewith.

Additional objects of the present invention will appear as the description proceeds.

The present invention overcomes the shortcomings of the prior art by providing a composite fiber made from natural and/or synthetic fibers having mineral compounds of various wavelengths and colors, such as opals, rubies, emeralds, sapphires, piezoelectric crystals and magnets forming an integral part of said fibers.

The methods of combining the gemstones with the natural/synthetic fibers includes encasing the mineral compounds within the natural/synthetic fibers by bonding the mineral compounds to the natural/synthetic fibers or laminating the mineral compound or compounds to the natural/synthetic fibers.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DETAILED DESCRIPTION OF THE PREFERRED EMBODIMENT

Figure 1:
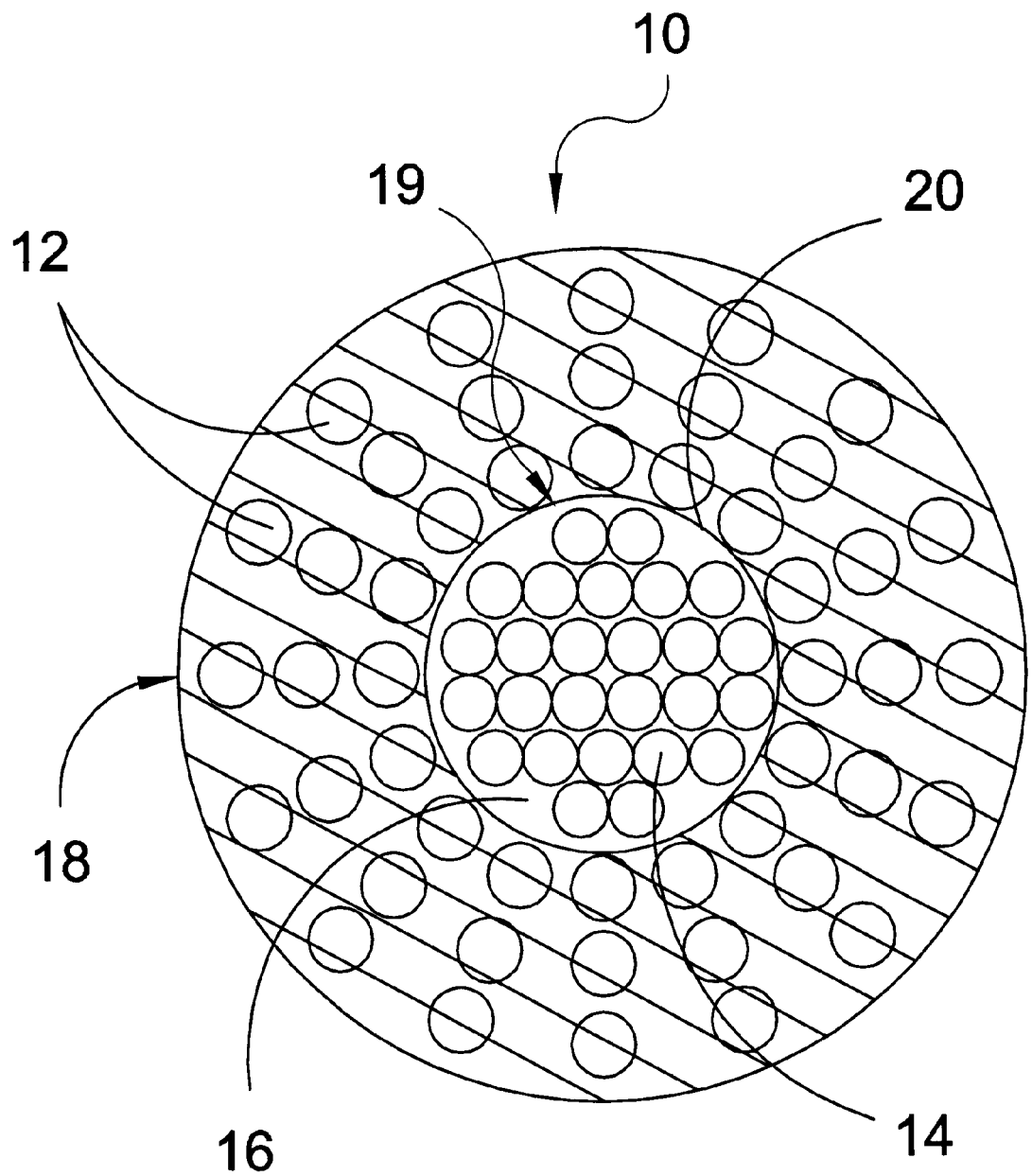
FIG. 1 is a sectional view of a mineral compound encased fiber of the present invention.

Turning now descriptively to the drawings, in which similar reference characters denote similar elements throughout the several views. With regard to the reference numerals used, the following numbering is used throughout the various drawing figures.

Figure 2:
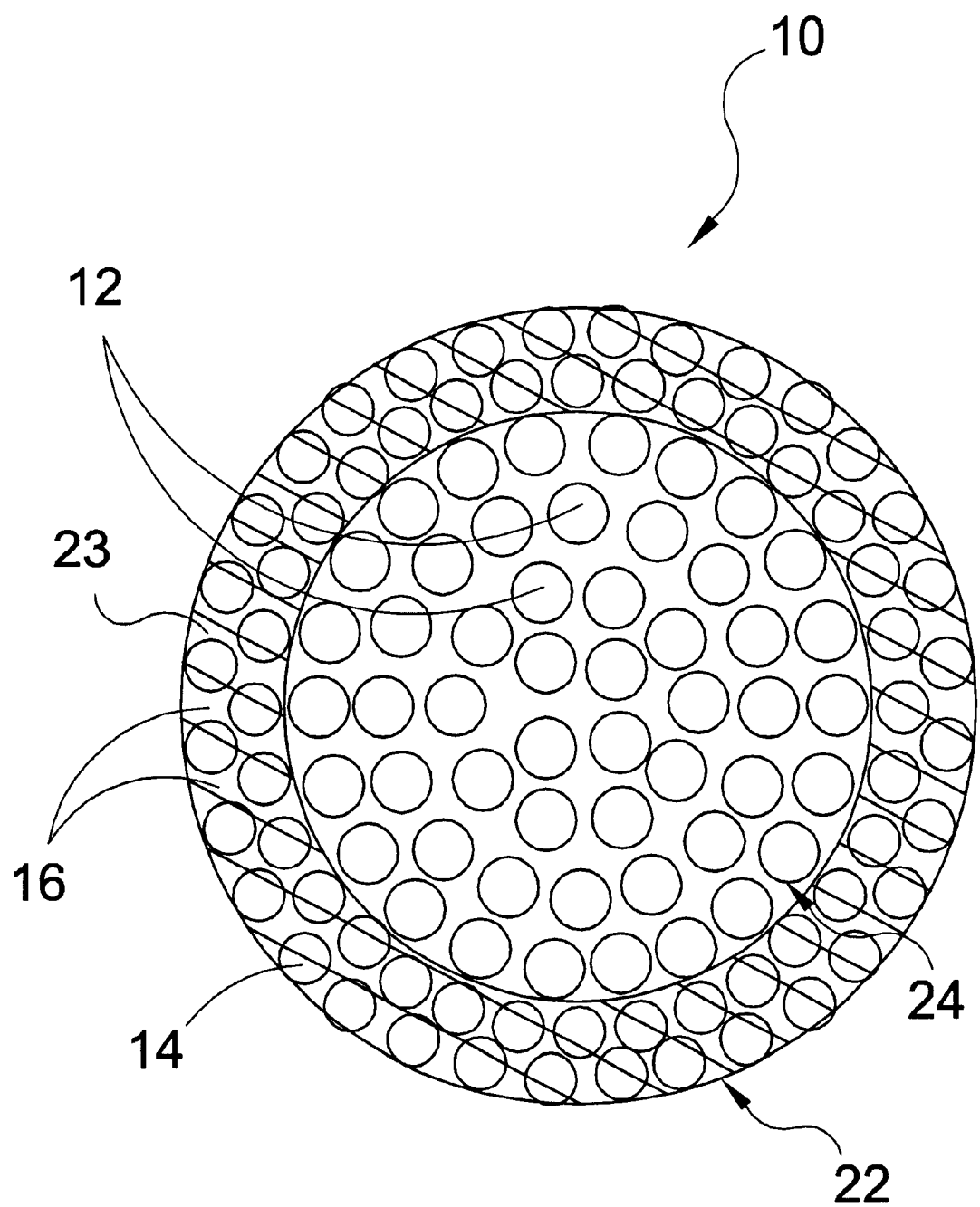
FIG. 2 is a sectional view of the laminated fiber of the present invention.

10 mineral compound composite textile material
12 fiber
14 mineral compound
16 cohesive agent
18 fiber-encased mineral compound
19 mineral compound core
20 extrusion mixture
22 mineral compound laminated fiber
23 resin
24 fibrous core
26 composite fiber speckled with mineral compound FIG. 1 is an illustration the mineral compound composite textile material 10 as a fiber-encased mineral compound 18 having mineral compounds 14 such as piezoelectric crystals, gemstones, colors and wavelengths and/or magnets encased within natural or synthetic fibers 12 such as cotton, wool, silk, hemp, jute, animal fur, or synthetic fibers. The yarn while having the outward feel and appearance of the exterior fibers would encase the properties of the enclosed minerals. The yarn can be used in weaving or knitting fabrics used in fashion wear or interior/exterior decor;

FIG. 2 is an illustration of a mineral compound composite textile material 10 as a mineral compound laminated fiber 22 manufactured having natural or synthetic fibers such as cotton, wool, silk, hemp, jute, animal fur, or synthetic fibers 12 encased within mineral compounds 14 such as piezoelectric crystals, gemstones, colors and wavelengths and/or magnets. The mineral compound laminated fiber 22 would have the appearance of the mineral compounds 14 while having the flexibility of the interior fibers 12.

Figure 3:
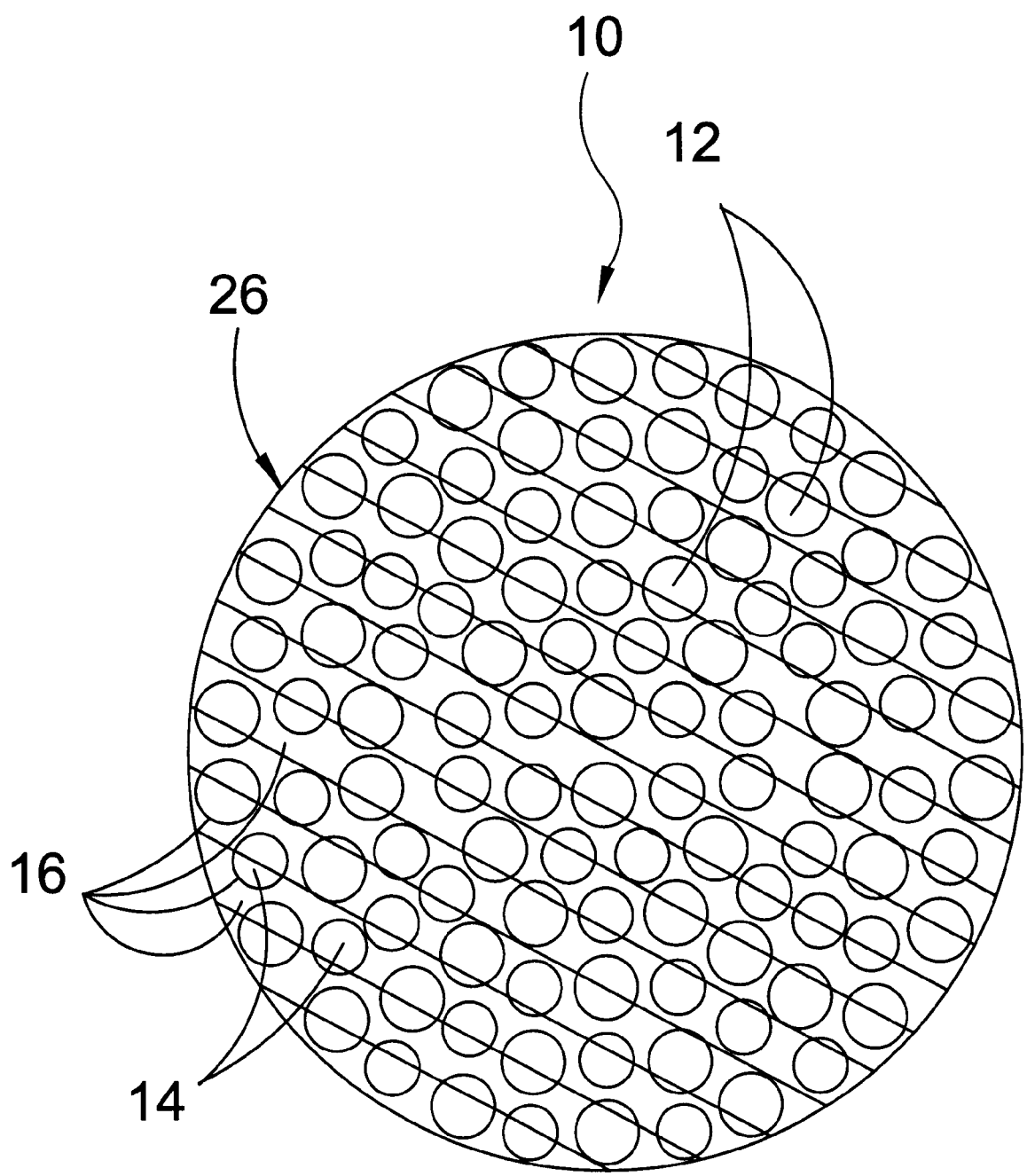
FIG. 3 is a sectional view of the blended fiber of the present invention.

FIG. 3 is an illustration of mineral compound composite textile material 10 as a composite fiber speckled with mineral compounds 26 dispersed within fibers 12. The processed mineral compound 26 has been blended with the cohesive agent 16 to form a slurry that was either applied to the fibers 12 or the fibers 12 had been bathed therein.

Figure 4:
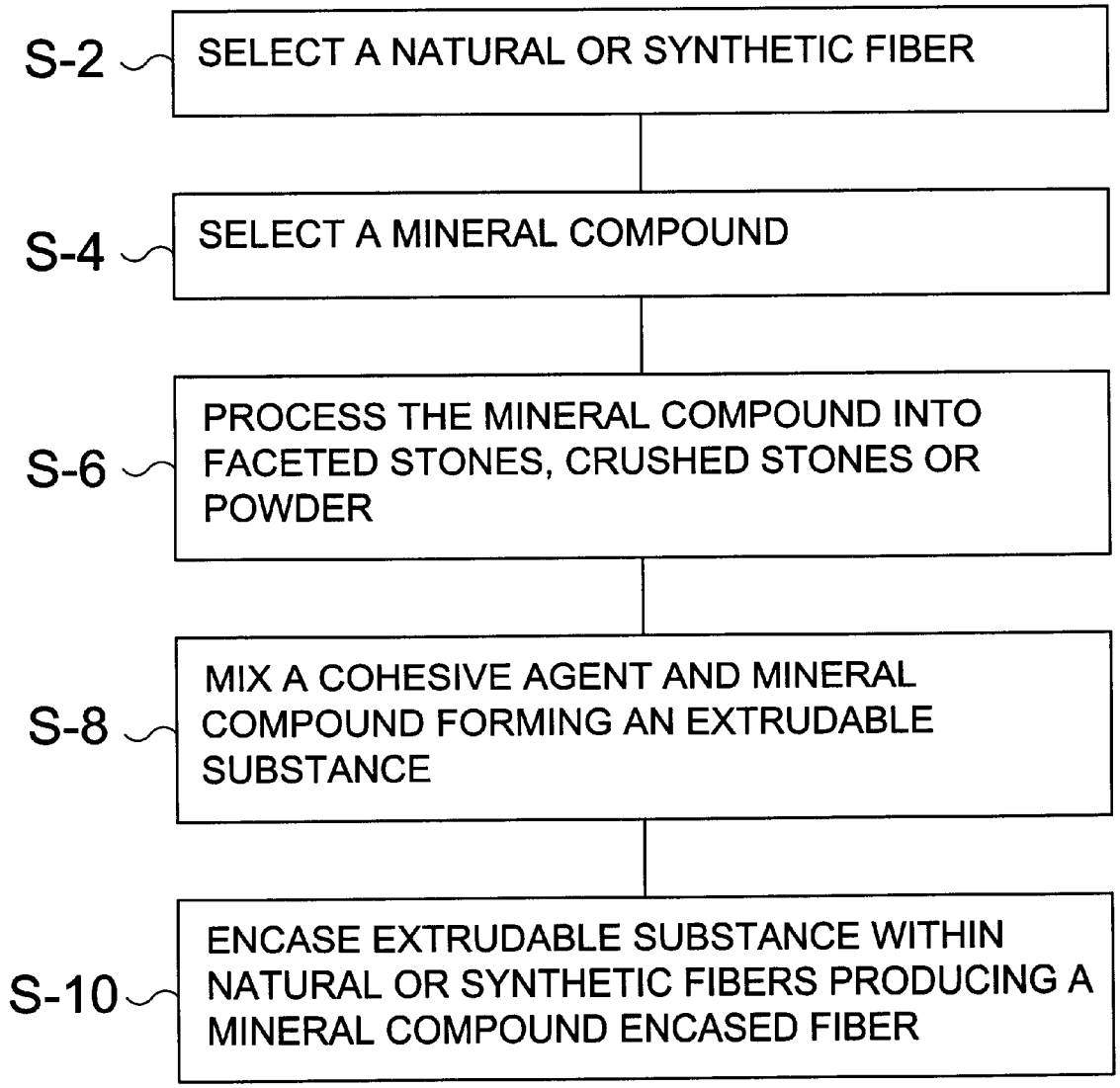
FIG. 4 is a flow chart of the manufacturing process for producing a composite fiber having a mineral compound core.

FIG. 4 is a flow chart of the manufacturing process for producing a fiber encased mineral compound 18. The fiber 12 is used to encase a mineral compound 14 that is combined with a cohesive agent 16 to create an extrudable mixture 20 which forms a mineral compound core 19.

Figure 5:
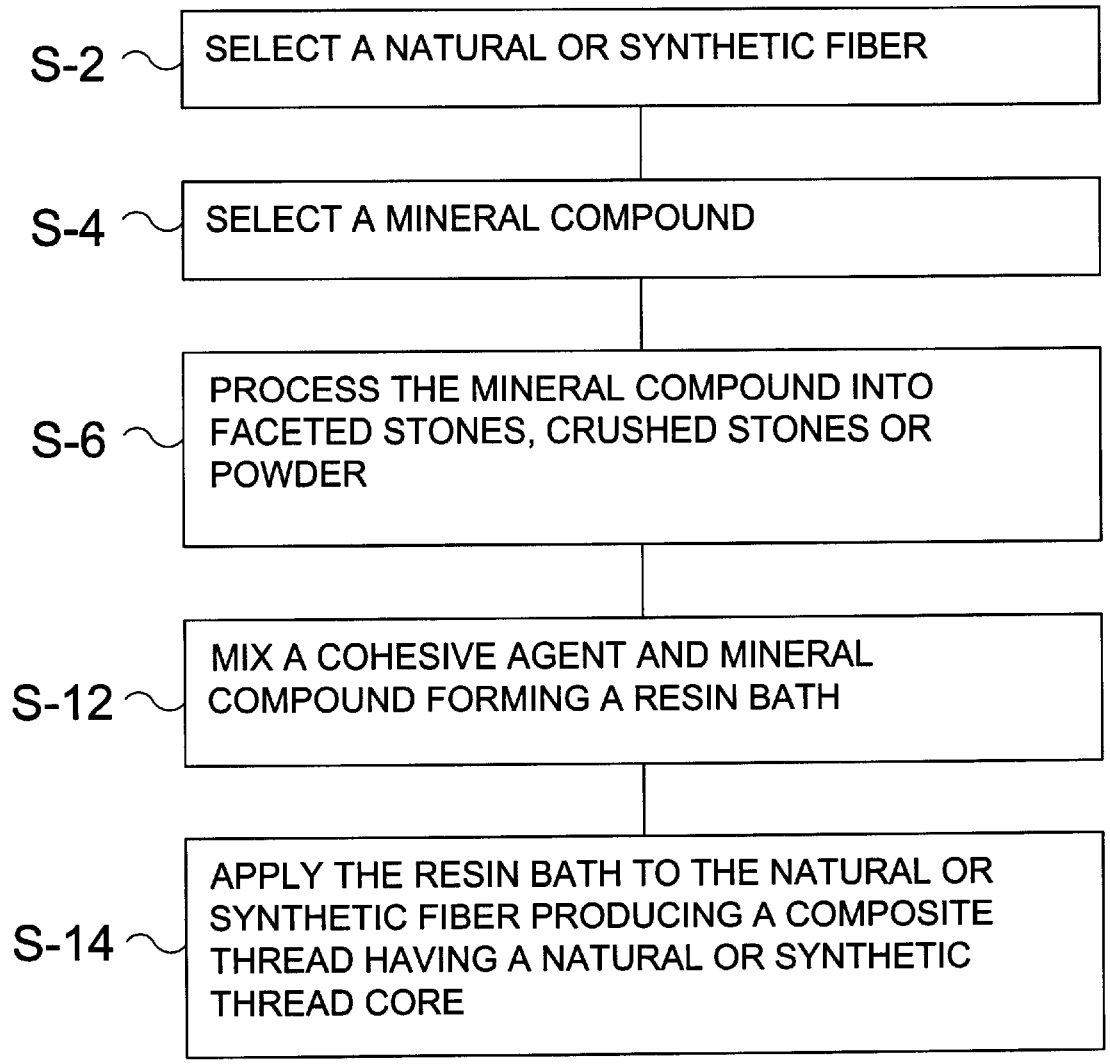
FIG. 5 is a flow chart of the manufacturing process for producing a composite fiber having a natural/synthetic fiber core.

FIG. 5 is a flow chart of the manufacturing process for producing a mineral compound laminated fiber 22. The mineral compound 14 is combined with a cohesive agent 16 to form a resin 23 that can be applied to the fibers 12 which then form a fibrous core 24. The resin 23 may include magnetic particles and/or piezoelectric crystals that are believed by many to have therapeutic properties.

Figure 6:
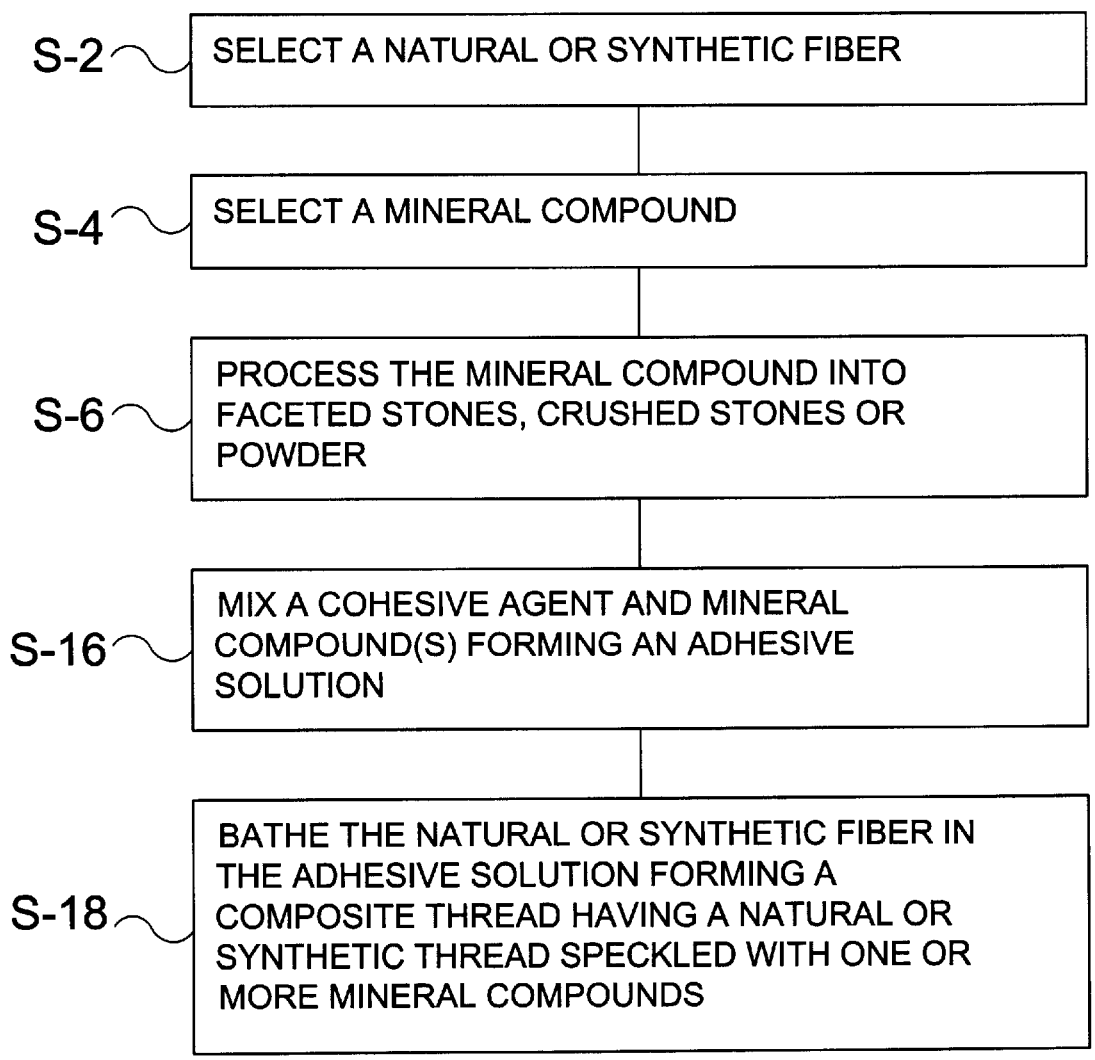
FIG. 6 is a flow chart of the manufacturing process for producing a composite fiber having mineral compounds and natural/synthetic fiber forming an integral part therewith.

FIG. 6 is a flow chart of the manufacturing process for producing a composite fiber speckled with one or more mineral compounds 26 wherein the mineral compound 14 is combined with a cohesive agent 16 to form a slurry that can be applied to fibers 12 or the fibers 12 could be run through a bath whereupon an amount of mineral compounds 14 will bond with the fibers 12. The slurry may include magnetic particles and/or piezoelectric crystals that are believed to have therapeutic properties.

What is claimed is new and desired to be protected by Letters Patent is set forth in the appended claims:

1. A method of manufacturing a mineral compound composite textile which comprises:
    a) selecting a natural or synthetic fiber suitable for use in a fabric;
    b) selecting one or more mineral compounds from the group consisting of magnets, gemstones and piezoelectric crystals;
    c) processing the selected mineral compound or compounds into faceted, crushed or powder form;
    d) mixing a cohesive agent and said mineral compound or compounds to form an extrudable substance;
    e) encasing said extrudable substance within said fiber producing an encased fiber suitable for use against a human body; and
    f) using said encased fiber to make a fabric usable to be worn or as a cover for furniture.

2. A method of manufacturing a mineral compound composite textile which comprises:
    a) selecting a natural or synthetic fiber suitable for use in a fabric textile;
    b) selecting a mineral compound from the group consisting of magnets, gemstones and piezoelectric crystals;
    c) processing said mineral compound into faceted, crushed or powder form;
    d) mixing a cohesive agent and said mineral compound forming a resin bath;
    e) applying said resin bath to said fiber producing a composite thread having a thread core; and
    f) using said composite thread having a thread core in the making of a textile to be worn by a person or to cover furniture.

3. A method of manufacturing a mineral compound composite textile material which comprises:
    a) selecting a natural or synthetic fiber suitable for use in a fabric;
    b) selecting one or more mineral compounds from the group consisting of magnets, gemstones, and piezoelectric crystals;
    c) processing the selected mineral compound or compounds into faceted, crushed or powder form;
    d) mixing a cohesive agent and said mineral compound or compounds forming an adhesive solution;
    e) bathing said fiber in said adhesive solution forming a composite thread having a thread sprinkled with said mineral compound; and
    f) using said composite thread in the making of fabric clothing for a person or as a cover for furniture.

* * * * *